United States Patent [19]

Garrison

[11] 4,251,453
[45] Feb. 17, 1981

[54] PRODUCTION OF ALUMINUM ALKYLS

[75] Inventor: Harry D. Garrison, Sulphur, La.

[73] Assignee: Conoco, Inc., Ponca City, Okla.

[21] Appl. No.: 68,779

[22] Filed: Aug. 22, 1979

Related U.S. Application Data

[63] Continuation-in-part of Ser. No. 11,607, Feb. 12, 1979, abandoned.

[51] Int. Cl.$^3$ .............................................. C07F 5/06
[52] U.S. Cl. ................................................ 260/448 A
[58] Field of Search .................................... 260/448 A

[56] References Cited

U.S. PATENT DOCUMENTS

| | | | |
|---|---|---|---|
| 2,863,894 | 12/1958 | Smith | 260/448 A |
| 2,900,402 | 8/1959 | Johnson | 260/448 A |
| 2,987,534 | 6/1961 | Shapiro et al. | 260/448 A |
| 3,000,919 | 9/1961 | Wetroff et al. | 260/448 A |
| 3,030,401 | 4/1962 | Movsovic et al. | 260/448 A |
| 3,032,574 | 5/1962 | Ziegler et al. | 260/448 A |
| 3,050,540 | 8/1962 | Gould | 260/448 A |
| 3,076,006 | 1/1963 | Kinter et al. | 260/448 A |
| 3,207,770 | 9/1965 | Ziegler et al. | 260/448 A |

*Primary Examiner*—Helen M. S. Sneed
*Attorney, Agent, or Firm*—Cortlan R. Schupbach, Jr.

[57] ABSTRACT

An improved method is disclosed for continuously purifying crude aluminum alkyls containing solid contaminants such as aluminum particles comprising passing crude aluminum alkyls into a first holding vessel, the contents of said vessel being continuously passed under pressure through a tubular filter having an upstream inner surface and a downstream outer surface, solids-containing aluminum alkyls passing through said tubular filter returning to the holding vessel, and purified aluminum alkyls passing through the filter wall exiting through the downstream outer surface, and recovered; monitoring the solids content of the holding vessel and ceasing crude aluminum alkyl flow into said holding vessel when solid contents reach undesirably high levels, thereafter passing said crude aluminum alkyls into an alternate holding vessel and filter, then further passing the contents of said first holding vessel through said tubular filter until substantially all remaining aluminum alkyls have passed through the filter to recovery, and purging the contents of said first holding vessel before filtration is resumed.

9 Claims, 3 Drawing Figures

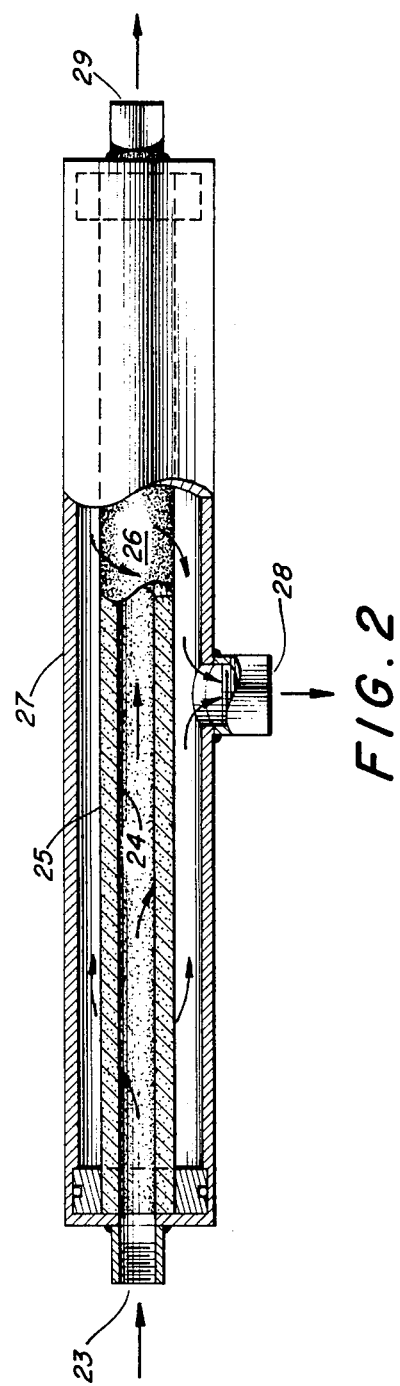

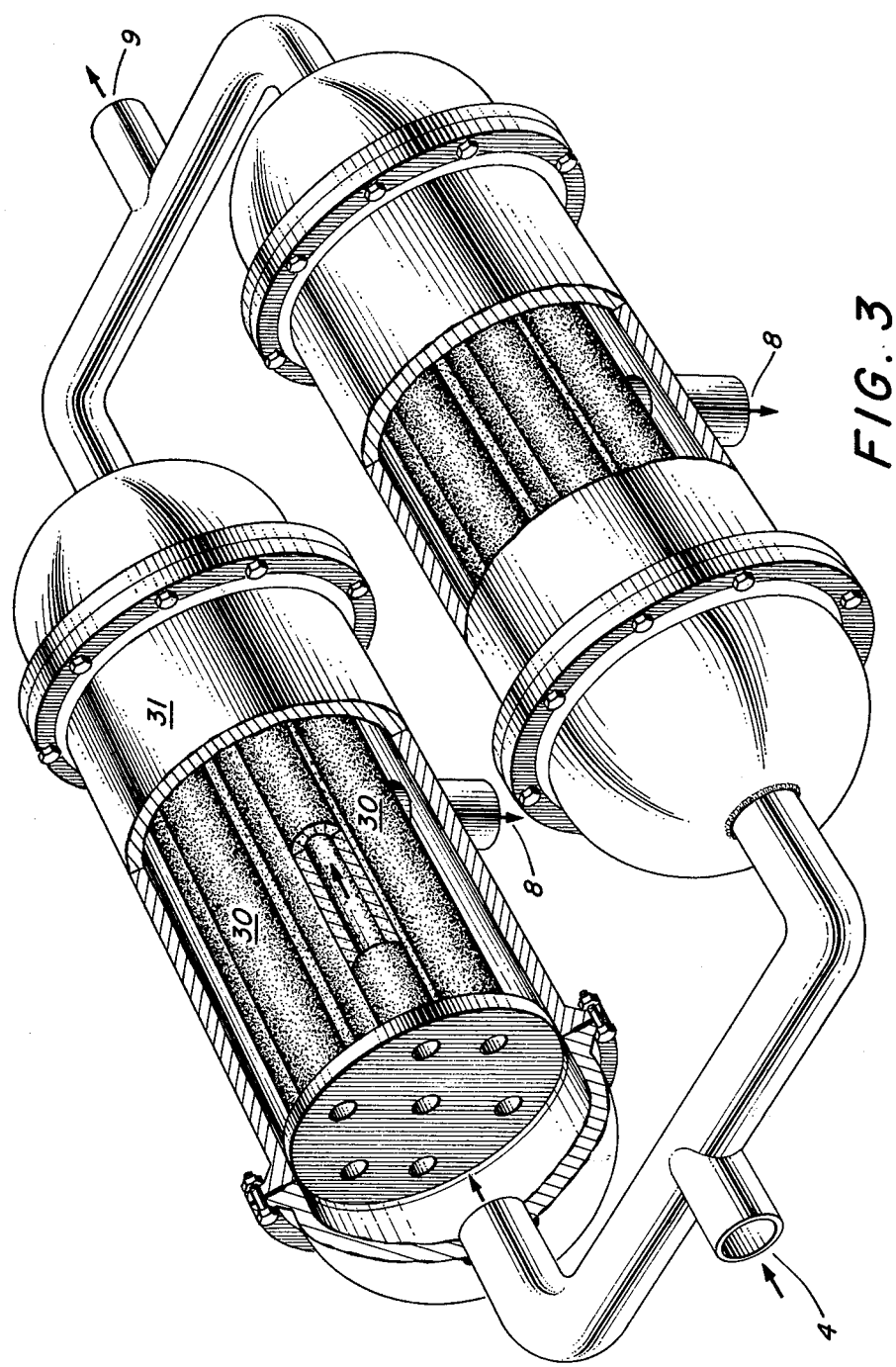

PRODUCTION OF ALUMINUM ALKYLS

This application is a continuation-in-part of U.S. Ser. No. 11,607 filed Feb. 12, 1979, now abandoned.

This invention relates to an improved method for continuously purifying crude aluminum alkyls containing solid particulate contaminants. More particularly, this invention relates to an improved method for continuously purifying crude aluminum alkyls by utilizing alternate tubular filter systems in order to provide continuous high quality recovery of aluminum alkyls.

Synthetic fatty alcohols have long been known. Initially, these alcohols were prepared from triglycerides found in natural animal fats and vegetable oils. These triglycerides were converted to corresponding methyl esters, and alcohols were formed by catalytic hydrogenation or by sodium reduction of the esters. Alcohols of the same structure are produced synthetically via Ziegler chemistry. In this process an olefin (usually ethylene), is polymerized onto triethyl aluminum in a "growth reaction" to produce higher straight chain aluminum alkyls. Oxidation of aluminum alkyls yields the corresponding alkoxide and hydrolysis of the alkoxide results in formation of the corresponding alcohol. Alcohols prepared by this procedure are interchangeable with natural alcohols in most uses.

Most commercial alcohol processes utilizing Ziegler chemistry utilize a growth reaction, adding ethylene to diethyl aluminum hydride to manufacture normal primary alcohols with an even number of carbon atoms in each chain. However, the nature of the materials handled throughout the process creates many problems. Dense slurries of aluminum and aluminum triethyl (ATE) and solvent must be handled in pipelines and pumped at high pressures. ATE burns on contact with air and decomposes explosively in the presence of water and thus can be very dangerous if not properly handled. Dilution of ATE with solvent makes handling somewhat less dangerous but care must still be taken to prevent spills or leaks of any plant stream which contains aluminum alkyls. Usually, all vessels and tanks containing aluminum alkyls are blanketed with an inert gas from a highly reliable source.

Raw material feedstocks to this process are aluminum powder, ethylene, and hydrogen. Crude aluminum alkyl, usually aluminum triethyl, is produced from aluminum powder, hydrogen, and ethylene. The crude product consists of aluminum alkyls, most of which are aluminum triethyl, a solvent diluent such as kerosene, and a finite amount of solid contaminants such as aluminum fines. These solid contaminants must be removed in order to obtain a product suitable for subsequent uses such as a growth reaction. The presence of these solid contaminants in the crude aluminum trialkyl (ATA) stream causes it to have a very dark or black appearance.

Generally described, two reactions are carried out to obtain the crude aluminum trialkyl. First, a slurry of fresh and recycled aluminum powder in aluminum alkyl and solvent is reacted with hydrogen to produce a product having a high aluminum dialkyl hydride (ADAH) content as product slurry in the hydrogenation reactor. The ADAH is then reacted with an olefin in an alkylation reactor to yield primarily aluminum trialkyl. A portion of the alkylation reactor product slurry is then recycled to provide feed to hydrogenation. The remainder of the alkylation reactor slurry is normally reduced in aluminum fine content by methods well known to those skilled in this art, such as centrifugation. The product stream containing the net aluminum alkyls produced in the process is the crude aluminum alkyl product (predominantly trialkyls) which is purified in accordance with the instant invention.

These reactions take place as follows, using ethylene as alkyl:

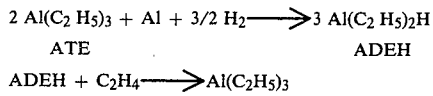

$$2\ Al(C_2H_5)_3 + Al + 3/2\ H_2 \longrightarrow 3\ Al(C_2H_5)_2H$$
$$\text{ATE} \hspace{4cm} \text{ADEH}$$

$$ADEH + C_2H_4 \longrightarrow Al(C_2H_5)_3$$

The crude aluminum trialkyl will contain unreacted aluminum fines and other solid impurities as solids. Normally, the level of these impurities is approximately 1% after centrifugation. These impurities must be removed before the crude aluminum alkyls can be used for most purposes.

Filters are known for removing aluminum fines from crude aluminum trialkyls to produce relatively pure ATE.

Representative but not exhaustive of such prior art is U.S. Pat. No. 2,863,894 which at column 3 beginning at about line 43 shows that aluminum alkyls can be filtered and used directly as polymerization catalysts. U.S. Pat. No. 2,900,402 shows that aluminum diethyl hydride present after a hydrogenation reaction can be filtered or decanted to remove aluminum fines. U.S. Pat. No. 2,931,820 discloses that aluminum alkyls can be prepared by reacting aluminum with primary alkyl halides to form a sesquihalide, then reacting said sesquihalide with an alkali metal to produce an aluminum alkyl which is subsequently purified by filtration. U.S. Pat. No. 2,987,534 shows removal of suspended aluminum by centrifuging. U.S. Pat. No. 3,000,919 relates to a process for producing organo aluminum compounds, and retention of metal within the reactor by a fine screen. However, in most aluminum trialkyl processes, the aluminum fines are too small to be removed by screening.

U.S. Pat. No. 3,030,401 shows a removal of unreacted aluminum powder by filtering the reaction solution in the presence of a filter aid such as bentonite clays. U.S. Pat. No. 3,032,574 discloses that the liquid product from the reactor has a dark appearance from suspended aluminum impurities, and teaches the removal of such impurities by centrifuging, vacuum distillation or filtration. U.S. Pat. No. 3,050,540 relates to a method for making aluminum alkyls and discloses that excess aluminum can be withdrawn and filtered for use in subsequent treatments. U.S. Pat. No. 3,076,006 relates that suspended solids can be removed by filtration. U.S. Pat. Nos. 3,207,770; 3,207,772; 3,207,773; and 3,207,774 all disclose that suspended aluminum in aluminum trialkyl products can be removed by distillation, centrifuging, or filtration.

However, these filters have proven highly dangerous and unreliable due to constant plugging, need for replacement, and cracking under high pressures, resulting in aluminum alkyl spills which are extremely hazardous both to personnel and equipment. Thus, in commercial operations the use of filters has been largely discontinued.

Purification of crude aluminum trialkyls has been carried out by vacuum distillation towers in place of filters in most current commercial operations. The crude aluminum trialkyl, containing solid contaminants such as aluminum fines and solvent, is charged into an aluminum trialkyl distillation tower. A clear, solid-free product containing primarily aluminum trialkyl and solvent is distilled overhead. The bottom product from the tower is charged to a second aluminum trialkyl solvent distillation tower. The second tower operates similarly to the first tower except that heavy solvent is added to improve the recovery of the aluminum trialkyl. Again, a clear solids free product containing primarily aluminum trialkyl and solvent is distilled overhead. The overhead product streams from the two towers are combined, filtered, and stored as finished aluminum trialkyl feed for subsequent reaction, or use. The bottoms product from the aluminum trialkyl solvent tower is directed to a quench reactor where the bottoms product is contacted with water in a "drowning" reaction to destroy the unrecovered waste aluminum alkyls before recovering the solvent. The use of such distillation systems is highly wasteful, both in energy and lost product, and is used primarily for safety considerations. It is well recognized that filtration is a preferred means if the unit can be operated safely, continuously, and provide a sufficiently high purity aluminum alkyl.

It would therefore be of great benefit to provide a continuous filter system which would produce a substantially solids free purified aluminum trialkyl stream at the desired aluminum trialkyl concentration in solvent while providing sufficient safety considerations for commercial implementation.

It is therefore an object of the instant invention to provide a process for producing finished aluminum trialkyls by removing aluminum fines and other solid impurities therein in a safe and continuous method.

The instant invention provides a method for producing aluminum alkyls substantially free of solid particulate contaminants comprising (a) reacting particulate alumina with hydrogen and lower olefin to obtain a crude aluminum alkyl reaction product, (b) passing the crude aluminum alkyl reaction product of (a) into a holding vessel and continuously circulating the crude aluminum alkyl reaction product from said holding vessel through a tubular filter having a tubular filter having a microporous wall, unfiltered material returning to said holding vessel while simultaneously recovering aluminum alkyls substantially free of solid contamination from the downstream outer surface of the microporous wall of the tubular filter. The contents of said vessel are continuously passed under pressure through the tubular microporous filter which has an inner surface representing the upstream side and an outer surface representing the downstream side, fluid exiting said tubular filter without passing through the filter wall returning to the holding vessel while purified aluminum alkyls passing through the wall and exiting through the downstream outer surface are recovered. In practice it is necessary to monitor the solids content of the holding vessel and cease crude aluminum alkyl flow into said holding vessel when said solids reach undesirable levels, thereafter passing said aluminum alkyls to a second holding vessel and filter; then continuing to pass the contents of said first holding vessel through said tubular filter until substantially all remaining aluminum alkyls have passed through the filter and have been recovered, and (c) purging the contents of said first holding vessel.

Briefly, FIG. 1 schematically shows the alternate filter systems used and is the best mode contemplated.

FIG. 2 is a cut-a-way view of a single filter.

FIG. 3 is an alternate embodiment showing the use of multiple filters within a common housing.

Figure 1:
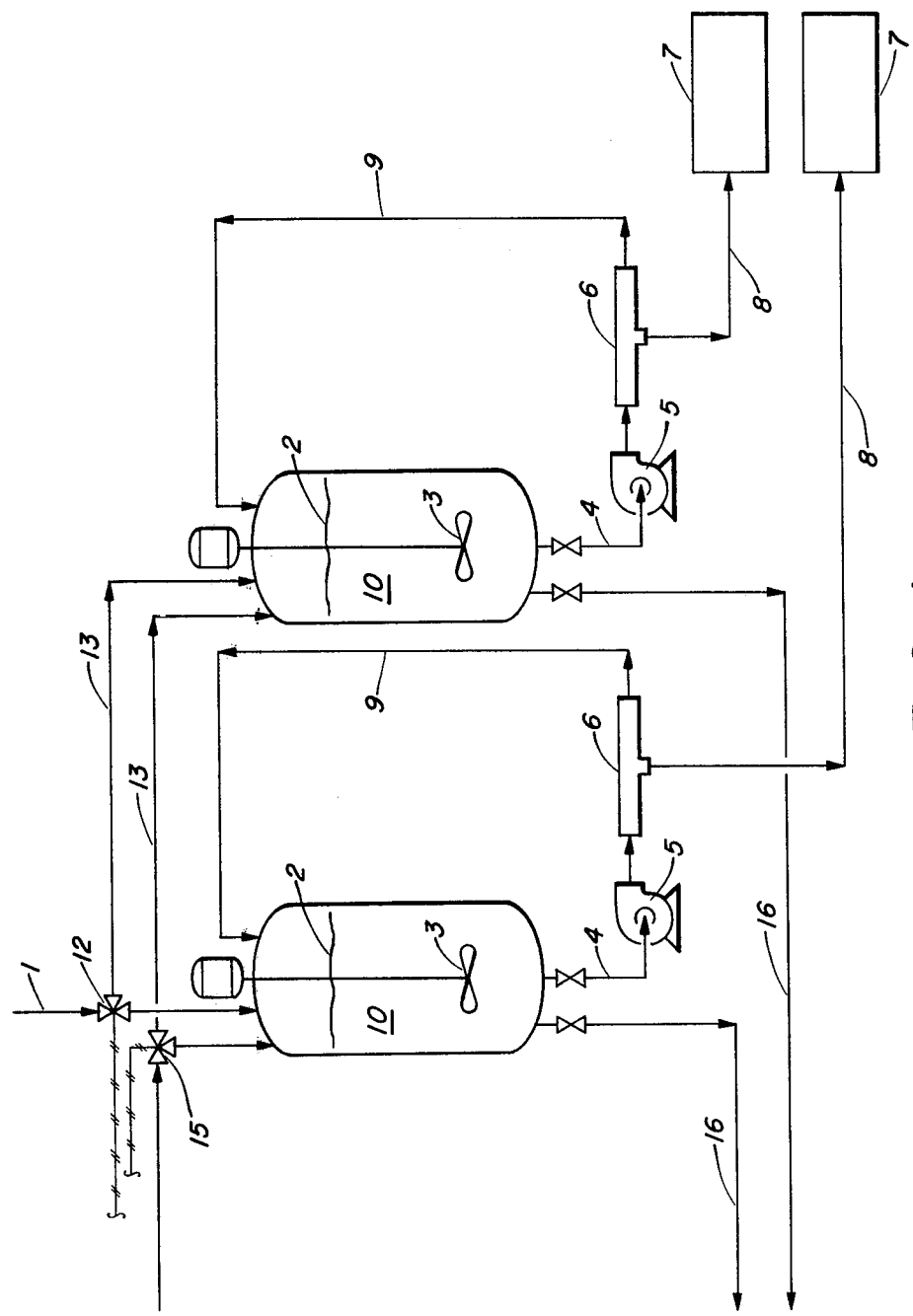

The instant invention is more concretely described with reference to the figures which show the alternating filter systems as used. The best mode of the instant invention is exemplified in FIG. 1. In the preferred embodiment, incoming line 1 contains the crude aluminum alkyls as obtained from the reaction of aluminum, hydrogen and olefins. These alkyls contain unreacted aluminum fines and other solid contaminants up to about 4% by weight. The stream passes through line 1 into a crude product holding vessel (2) which is continuously agitated by agitating means (3). The contents of the holding vessel are continuously withdrawn through a line (4) and forced by a high pressure pump (5), through a filter apparatus (6). Filtered, purified aluminum trialkyls are sent to a storage area (7) downstream of the filter through line (8). Unfiltered product containing solid contaminants and aluminum alkyls are returned to the holding vessel through line (9). The contents of the holding vessel (10) are continuously monitored until an undesirably high level of solids is obtained. Once this has occurred, valve (12) is closed and the crude aluminum trialkyl is sent to an alternate product holding vessel through line (13), and the alternate filter system begins operation.

While the filter of the alternate system is in operation, solvent diluent enters the first product holding vessel through line (15) and the pump (5) continues circulating the contents of the first product holding vessel through the filter, together with the solvent diluent, until substantially all aluminum alkyls have passed through the filter and the crude product holding vessel contains only aluminum fines and other solid contaminants in solvent. During the filtration, the reduced amount of purified aluminum alkyls and solvent passes through line (8) to produce storage (7). Initial aluminum alkyl concentration in product storage (7) will be from about 75 to 85% aluminum alkyls. However, because of subsequent solvent diluent addition due to the removal of substantially all aluminum alkyls from the first holding vessel, the total content of the storage system at the conclusion of filtration will be from about 55 to about 65% by weight. Normally, sufficient solvent will be added to replace the volume of aluminum alkyls collected through the filters, such that the volume of the holding vessel is substantially unchanged. After all alkyls are removed, additional solvent flow to the holding vessel is ceased, and most solvent can also be recovered through the filter.

After substantially all aluminum alkyls have been removed from the first product holding vessel (during which time the crude aluminum alkyl stream is being purified by the alternate filter system), the first crude product holding vessel is pumped to disposal, normally a hydrolysis reactor, through line (16). The crude product holding vessel is then normally rinsed with a small amount of solvent and held in readiness for resumption of filtration once the alternate crude product holding vessel reaches undesirable levels of solid content.

The system is simple, efficient and provides continuous safe operation. Filters suitable for this use are known and can be made according to the process described in U.S. Pat. No. 4,088,576, hereby incorporated by reference.

Concisely described, filters useful in the instant invention are tubular filters having an upstream inner surface and a downstream outer surface, said filter being incorporated within a housing to collect filtered product on the downstream side of the filter. As the unfiltered material is passed through the filter under high pressure from a crude product holding vessel, a small portion of the product will pass through the walls of the filter and be collected within the housing, the portion of the product which did not pass through the filter being returned to the holding vessel and subsequently again passing through the filter, at which time a portion of the remaining product passes through the filter wall. The filter has the advantage of being continuous, yet trouble-free, since the velocity of fluid flow across the filter surface substantially avoids blockage of the filter.

The addition of crude aluminum alkyls to the holding vessel as filtration progress is continued until an undesirably high level of solid contaminates is reached, at which time the crude aluminum alkyls are passed to the alternate holding vessel. Normally undesirable levels of contaminates are up to about 20% by weight, but passage to the alternate system is preferably made when solids levels reach from 10 to about 16% by weight.

FIG. 2 is a cut-a-way view of an acceptable filter system showing a single tube within a housing. The direction of flow is illustrated by the arrows. Flow from the holding vessel enters the inertial filter at (23). There is a high differential pressure between the inner upstream surface of the filter (24) and the downstream outer surface of the filter (25). Fluids passing through the filter itself (26) are collected by a housing (27) and passed through a line (28) to a purified aluminum alkyl storage. Unfiltered aluminum alkyls and aluminum fines which cannot pass through the filter return to the holding vessel (29).

When used for aluminum alkyls, the microporous wall of the filter will normally have a pore size of from about 0.5 to about 10 microns. In commercial operations, pore sizes of from about 2 to 5 microns will normally be used. Larger pore sizes are preferred to allow more rapid filtration, but the removal of solid contaminants is the primary consideration.

Such filter systems can also be equipped with a backflush in order to clear the filter surface between holding vessel purgings. Such backwash operations are most conveniently carried out with an inert gas under pressure. Examples of such gases are nitrogen and argon. Solvent backwashes could be used, but are not preferred.

The filter itself is tubular, or a similar closed configuration, but a choice of materials is available for the composition. Materials such as glass, ceramic and metal can be used, as well as combinations of these. The material used must be able to withstand the differential pressure employed. Filters of the type described in the incorporated U.S. Pat. No. 4,088,576 are particularly suitable for use in the invention.

FIG. 3 describes multiple filters in either series or parallel. Additionally, the Figure describes multiple filters (30) encased within a common housing (31). Such an apparatus has an appearance substantially similar to a heat exchanger apparatus wherein the filter would correspond to a heat exchanger tube and the housing would surround a bundle of filters. Likewise, several bundles of filters can be used either in series or in parallel in order to obtain the purified aluminum alkyl. The crude aluminum trialkyl stream is passed via line (4) to multiple housing, each containing multiple filter tubes. Filtered aluminum alkyl is then passed (8) to storage while unfiltered alkyls return to the holding vessel via line (9). Although the filters are shown in a parallel configuration, a series configuration, or a combination of series and parallel, can also be used.

It should likewise be realized that while the Figures describe only two alternating filter systems, more than two can, of course, be used if so desired or necessary. For example, three or more systems could be used wherein a first system would be filtering crude aluminum alkyls, a second system would be undergoing final filtration of residual aluminum alkyls in the holding vessel, and a third system would be recovering solvent from the holding vessel after substantially all aluminum alkyls had been recovered. If filtration time is too long, a fourth system could, for example, be added in order to allow time for flushing and disposal of the holding vessel and filter system prior to resumption of filtration of the crude aluminum alkyl stream.

Thus, the instant invention involves at least two parallel filter systems with product holding vessels which alternate using a simple three step process;

(a) concentration of solids of crude aluminum alkyls from 0.5 to about 15% by weight in a holding vessel followed by (b) dilution of aluminum alkyls to less than 0.1% by weight aluminum alkyls in said holding vessel, completed by (c) discharge of the high solids content holding vessel residue to a disposal site, usually a hydrolysis quench reactor.

The advantages of such a system are clear. Large amounts of aluminum alkyl losses from distillation and cleaning of other type filters can be avoided. Energy consumption for distillation towers can be drastically reduced on the order to billions of BTU's per year for commercial facilities. Solids waste disposal will be cut by a large fraction since aluminum alkyls are not destroyed along with the solvents. Down time for turn arounds is eliminated as well as the need for crude aluminum alkyl storage. The system also allows constant aluminum alkyl feed to subsequent sections which allows more stable operation and optimization of subsequent processes. In addition, the process improves safety by reducing the hazard associated with cleanouts, turnarounds, and breakdowns.

Other methods of filtration or separation of aluminum from the aluminum alkyl stream can be utilized in conjunction with the instant invention. For example, it is preferable to use a centrifuge directly upstream of the filter alternating systems in order to recover useable aluminum which can then be recycled back to the initial reaction. Centrifuging can be adjusted so as to remove only the largest, most useable aluminum. Alternatively, multiple centrifuges could be used in order to remove first the useable aluminum and then remove subsequent amounts of solid contaminants as far as practical before passing on to the filter system. This would increase the length of time that a filter system could be used before switching to the alternate filter system while recovering residual alkyls from the first filter system.

In an alternate embodiment, all or a portion of the high solids content in the holding vessel is returned to the preparation of ADAH so that previously unreacted, active aluminum can be utilized. However, in practice it will be necessary to totally purge the holding vessel from time to time to remove unreactive aluminum fines and other solid contaminants. Usually such total disposal will occur from about every second filter cycle to about every tenth filter cycle, depending on reaction conditions used and levels of solid contaminates in the filter system.

Lower olefins as used herein is meant to indicate olefins having from 2 to 12 carbon atoms and contains both primary and internal olefinic bonds. Aluminum alkyls as used herein is meant to indicate materials formed from the reaction described, and Ziegler chemistry in general, including aluminum alkyls, aluminum dialkyl hydrides and halides, and aluminum trialkyls.

Representative but non-exhaustive examples of olefins useful in the reactions described are ethylene, pentene, butene, isobutene, propylene, hexene, heptene, nonene, decene, and dodecene. Representative but non-exhaustive examples of aluminum alkyls are aluminum diethyl hydride, aluminum triethyl, aluminum diethyl chloride, aluminum trihexyl, aluminum ethyl butyl hydride and aluminum tributyl.

Solvents useful in the method of the instant invention are those free of nitrogen, oxygen, and sulfur. Preferably, but not critically, the solvent should also be free of alkene bonding. Representative but non-exhaustive examples of suitable solvents are kerosene, gas oil, hexane, octane, isooctane, dodecane, xylene, benzene, low polynuclear aromatic (LPA) solvents and mixtures of paraffinic and aromatic solvents.

The invention is more concretely described with reference to the example below, wherein all parts and percentages are by weight unless otherwise specified. The example is provided to illustrate the instant invention and not to limit it. The filter unit used was the FIG. 2 single tube filter.

EXAMPLE 1

The process of the instant invention for removing aluminum solids from crude ATE was successfully tested in pilot unit operations. A portion of commercial crude ATE product stream was fed to the pilot unit from a commercial facility. A test run of 0.3 to 0.4 gallons per minute (gpm) of crude ATE was fed to the pilot unit surge drum, while the same amount of solids-free filtrate was removed as effluent from the filter. The stream contained approximately 0.5% solids by weight, and was at a temperature of 120° to 150° F. The crude ATE from the surge drum was pumped through the inertial filter and back into the drum at a flow rate of 75 to 100 gpm. The inlet pressure on the filter mainstream circulation was 50 pounds per square inch gauge (psig) and the outlet pressure was 45 psig. During the course of the test run the aluminum solids accumulated in the surge drum until the drum contained about 12% solids by weight. The crude ATE feed was then halted and pure kerosene solvent was fed into the surge drum while the clear filtrate flow of 0.3 to 0.4 gpm was continued from the filter. The solvent was fed until substantially all residual aluminum alkyls were pumped from the surge drum, leaving only the removed aluminum solids and solvents in the drum. Throughout the test run 70 to 110 psig nitrogen was used to backflush the inertial filter. This "blowback" was pulsed to pump the nitrogen back through the filter every 5 to 20 minutes with the nitrogen pulse lasting for 0.7 to 1.0 seconds.

The process of the instant invention removed aluminum solids from crude ATE with practically no alkyl losses. Losses were reduced to 0.03 to 0.04% of feed, compared to 3 to 5% of feed for distillation in the commercial plant. This reduction in aluminum alkyl losses not only increased production but also reduced the waste stream that must be disposed. A substantial energy savings was realized with the process of the instant invention and consumed only about 200 BTU per pound of ATE product, compared to 1400 to 1500 BTU for the commercial facility.

It is apparent that the instant invention offers many advantages over the prior art methods of filtration, distillation, centrifugation, and other methods of separation. The system is continuous, provides a high purity aluminum alkyl, allows the selection of various filter sizes, and likewise allows lower energy costs, increased recovery of aluminum alkyl products with increased safety to personnel because of turnaround elimination.

While certain embodiments and details have been shown for the purpose of illustrating this invention, it will be apparent to those skilled in this art that various changes and modifications may be made herein without departing from the spirit or scope of the invention.

I claim:

1. A method for producing aluminum alkyls substantially free of solid contaminants, comprising
   (a) reacting aluminum, hydrogen and lower olefins to obtain a crude aluminum alkyl reaction product containing solid contaminants,
   (b) passing the crude aluminum alkyl reaction product into a holding vessel under inert pressure while
   (c) continuously circulating the crude aluminum alkyl reaction product from said holding vessel through a tubular filter having a microporous wall, unfiltered reaction product returning to said holding vessel, while recovering aluminum alkyls substantially free of solid contaminants from the outer downstream surface of the microporous wall of the tubular filter.

2. A method as described in claim 1 wherein the solids content of the holding vessel does not exceed 15%.

3. A method as described in claim 2 wherein solvent is added to the first holding vessel in place of crude aluminum alkyl feed in a quantity sufficient to maintain vessel content volume as aluminum alkyls are withdrawn through said filter.

4. A method as described in claim 3 wherein the recovered purified aluminum alkyls are passed to a holding vessel.

5. A method as described in claim 4 wherein the aluminum alkyl is aluminum trialkyl and wherein purified trialkyls in said holding reservoirs are diluted with solvent until purified aluminum trialkyl is at a concentration of about 60% aluminum alkyls by weight in said holding reservoir.

6. A method as described in claim 3 wherein a tubular filter is periodically backflushed with an inert gas to remove filtercake buildup on the inner upstream surface.

7. A method as described in claim 6 wherein the inert gas is selected from the group consisting of nitrogen and argon.

8. A method as described in claim 3 wherein more than one tubular filter is disposed within a common housing.

9. A method as described in claim 1 wherein aluminum, hydrogen and recycled aluminum alkyls are reacted in a first reaction zone to produce an intermediate reaction product which is then reacted with lower olefins in a second reaction zone to produce the crude aluminum alkyl reaction product containing solid contaminants.

* * * * *